United States Patent
Harre et al.

(10) Patent No.: US 8,684,229 B2
(45) Date of Patent: Apr. 1, 2014

(54) DISPENSER AND METHOD FOR DISPENSING DENTAL MATERIAL

(75) Inventors: Manfred Harre, Landsberg am Lech (DE); Dirk Müller-Paul, Neubeuern (DE); Michael Keller, Gauting (DE); Ingo W. Wagner, Wörthsee (DE)

(73) Assignee: 3M Innovative Properties Company, St. Paul, MN (US)

( * ) Notice: Subject to any disclaimer, the term of this patent is extended or adjusted under 35 U.S.C. 154(b) by 840 days.

(21) Appl. No.: 12/282,177

(22) PCT Filed: Mar. 8, 2007

(86) PCT No.: PCT/US2007/063528
§ 371 (c)(1),
(2), (4) Date: Jun. 1, 2009

(87) PCT Pub. No.: WO2007/121003
PCT Pub. Date: Oct. 25, 2007

(65) Prior Publication Data
US 2012/0097702 A1 Apr. 26, 2012

(30) Foreign Application Priority Data

Mar. 10, 2006 (EP) .................................. 06004997

(51) Int. Cl.
*A61C 5/06* (2006.01)
(52) U.S. Cl.
USPC ............. 222/1; 222/135; 222/145.6; 222/333
(58) Field of Classification Search
USPC ............... 222/63, 94, 135–137, 145.5–145.8, 222/325–327, 333, 1
See application file for complete search history.

(56) References Cited

U.S. PATENT DOCUMENTS

| | | | | |
|---|---|---|---|---|
| 5,286,105 | A | * | 2/1994 | Herold et al. ............... 366/162.3 |
| 6,244,740 | B1 | | 6/2001 | Wagner et al. .............. 366/181 |
| 6,315,164 | B1 | | 11/2001 | Mühlbauer et al. ............. 222/63 |

(Continued)

FOREIGN PATENT DOCUMENTS

| | | | |
|---|---|---|---|
| DE | 41 06 388 | 9/1992 | ............... A61C 5/06 |
| DE | 199 51 504 | 5/2001 | ............. A61C 5/060 |

(Continued)

*Primary Examiner* — J. Casimer Jacyna (57) ABSTRACT

The present invention is preferably directed to a dispenser of the type sold by 3M ESPE under the trade name Pentamix and as also described above. Such a dispenser preferably comprises at least a first and a second compartment for a first reservoir and a second reservoir, respectively, the first and the second reservoirs containing a first and a second component for the dental material, respectively. It further preferably comprises a first and a second plunger driven by a first drive for advancing the first and the second components from the first and the second reservoirs, respectively. Moreover, a dynamic mixer driven by a second drive for automatically mixing the first and second components to form the dental material from the first and second components is provided. Such a dispenser further preferably has a dispensing portion or mixing tip for dispensing the mixed dental material. The present invention is more particularly directed to a dispenser or method adapted for advancing and mixing at least one dental material, comprising at least one drive which is operated on a predetermined, non-uniform drive speed profile. Preferably an advancing speed profile is provided for advancing the components and/or a mixing speed profile is provided for mixing the components, and either profile may be a "drive speed profile" as that term is used herein. More preferably both profiles are provided.

22 Claims, 5 Drawing Sheets

(56) References Cited

U.S. PATENT DOCUMENTS

| | | | |
|---|---|---|---|
| 6,631,829 B1 | 10/2003 | Wagner et al. | 222/23 |
| 6,854,349 B2 * | 2/2005 | Brandhorst et al. | 73/866 |
| 6,932,237 B2 * | 8/2005 | Heymann et al. | 222/1 |
| 2002/0064754 A1 | 5/2002 | Horth et al. | 433/80 |
| 2003/0022128 A1 | 1/2003 | Heymann et al. | 433/89 |
| 2004/0029772 A1 | 2/2004 | Konietzko | 514/1 |
| 2008/0264971 A1 | 10/2008 | Harre et al. | 222/137 |
| 2008/0308580 A1 * | 12/2008 | Gaydos et al. | 222/333 |
| 2012/0057425 A1 * | 3/2012 | Henniges et al. | 366/130 |

FOREIGN PATENT DOCUMENTS

| | | | |
|---|---|---|---|
| EP | 0 087 029 | 8/1983 | A61C 5/06 |
| EP | 0 492 413 | 7/1992 | B01F 15/02 |
| EP | 1 802 385 | 7/2007 | B01F 13/00 |
| JP | 08-215554 A | 8/1996 | |
| WO | WO 01/30488 A2 * | 5/2001 | B01F 13/00 |
| WO | WO 2005/084579 | 9/2005 | |

* cited by examiner

DISPENSER AND METHOD FOR DISPENSING DENTAL MATERIAL

Cross Reference to Related Applications

This application is a national stage filing under 35 U.S.C. 371 of PCT/US2007/063528, filed Mar. 8, 2007 which claims priority to European Patent Application No. 06004997.0, filed Mar. 10, 2006, the disclosure of which is incorporated by reference in their entirety herein.

TECHNICAL FIELD

The invention relates to a dispenser and a method for dispensing dental material. More particularly the invention relates to the mixing of pasty or highly viscous components to form a dental material, such as a multiple-component impression material used for making models of teeth.

DESCRIPTION OF THE RELATED ART

Dispensing devices with reservoirs or cartridges are often used in the field of dentistry for mixing and dispensing dental compositions of two or more components, such as impression materials, restoratives, adhesives, cements, etching gels, sealants and the like.

In one type of dispenser that comprises a cartridge, the dispensing device has a plunger that is advanced either manually by the user or automatically by a machine during a dispensing operation. Often, the plunger is received in an open end of the cartridge and bears against a piston within the cartridge. As the plunger is advanced to move the piston, the plunger expels or dispenses a quantity of material through a front outlet or opening of the cartridge.

The dispensing cartridge of such a device often comprises two cylindrical compartments arranged in parallel to each other. In each compartment a reservoir can be provided. Each reservoir contains a specific component, usually either a base paste or a catalyst paste. These two components are pressed from their respective reservoirs out into a mixing area, or tip, where the components mix to form the required dental material. The mixer may be a static mixer having stationery mixing structures or, preferably, a dynamic mixer having a rotary mixer element. The pressure further urges the mixture out of the mixing tip so that the dental professional can use it as desired.

For example, EP-A-0492413 discloses an apparatus for mixing and dispensing multiple-component substances. The apparatus includes a housing, a trough-shaped receptacle for a cartridge having compartments. The cartridge has a mixer head attached to the front ends of the compartments. Rigid plungers movably disposed in the cartridges, an electrical motor for driving the plungers, a mixer rotating shaft extending parallel to, and disposed between cartridges and having its front end engaging a mixer element rotatably supported within the mixer head, and an electrical motor for driving the shaft. The two plungers are rigidly interconnected at their back ends by a transverse member and are advanced in common by an electrical motor. In operation, a unit consisting of filled cartridges and a mixer head attached thereto is placed into the receptacle. The plungers are then slowly advanced within their respective cartridges so as to urge the two components into the mixer head. Simultaneous rotation of the mixer element causes the components to be mixed to form a ready-to-use substance which is forced out of a dispensing opening of the mixer head. After the desired amount has been dispensed, the apparatus is switched off. The disclosure of this document is incorporated by reference herein.

Another example of a dispensing device is an automatic dispensing system (e.g., a Pentamix™ dispensing device available from 3M ESPE AG) that includes a motor-driven mixing unit and reusable and interchangeable cartridges. The mixing unit comprises a chamber or compartment for holding the cartridge, and two parallel, motor-driven plungers designed to plunge into two respective compartments of the cartridge and to exert high pressure on the viscous components contained therein. The motor for the plungers provides high torque to extrude the viscous components under high pressure into a mixing tip. Furthermore, the motor also provides a reasonably high speed to rapidly move the plungers forward and backward within the cartridge when the viscous components are not being extruded. A DC motor is generally used in such devices. The motor drives the plungers into a back position for filling new components into the cartridge and/or inserting new cartridges of components into the machine. After refilling, the plungers are driven into a position wherein the plungers come in direct contact with the reservoirs or indirect contact with plungers provided at each end of a reservoir. When the plungers each contact a component or plunger, the resistance, and therefore the load, increases and a high load is applied to the driving gearbox and motor during the dispensing operation.

These kinds of multi-component dispensers generally ensure simultaneous movement of the driving members, especially when the mixing ratio of the material components is different from 1:1. For example, components for dental impression materials are often mixed at a ratio of 1:2 (or, in some cases 1:5). Due to such mixing ratios, it may be difficult to advance driving members synchronously. Also, with multi-component dispensers, the plungers of the driving members may have different cross-sectional areas, for example, to accommodate the respective cross-sectional areas of the material component compartments and to enable the application of different pushing forces necessary to dispense the material components from their individual chambers according to the desired mixing ratio. For example, for a 1:5 composition, the ratio of the pushing forces would be 1:25, assuming the pressure in both compartments is the same. Additionally, the material component forming the major part of the mixed material often contains fillers making it more viscous relative to the other material component, which increases the ratio of the forces beyond 1:25. This difference in the viscosities of the individual material components also influences the necessary pushing forces. Overall, this means that the load is different on the each of the driving members (including plungers) during expelling of the components.

Depending on the viscosity and mixing ratio, the fact that the pressure builds up differently in the individual cartridge cylinders when the device is started may cause the components to reach the mixer at different times. In such a case, the initial volume of paste dispensed from the mixer has a mixing ratio which differs from a desired value and may therefore cure less perfectly or more slowly, or have other undesired properties.

The 3M ESPE Company offered a dynamic mixer similar to the above described dynamic mixer of U.S. Pat. No. 6,244,740-B1, and a pair of first and second compartments fitting thereto and filled with catalyst paste and base paste, respectively.

DE 19951504 C2 relates to a device for producing dental compounds from two or more pasty constituents and/or liquid components. In said device, the rotational speed of a rotating element of a dynamic mixer can be controlled in a stepless manner using a control unit. In addition, the feed rate of plungers which engage in the cartridges can optionally be controlled independently of one another. The feed rate control is based on material characteristics of the individual constituents, which have been detected using information provided on the cartridges and/or based on predetermined characteristics such as viscosity and the setting time of the finished mixture which have been input using corresponding regulators. In this way, mixtures with different compositions and characteristics can be produced using a single mixing device, without modifying the constituents placed therein.

U.S. Pat. No. 6,315,164 B1 relates to a method and device for dispensing a multi-component compound, in particular for dental purposes, by pressing its components out from exchangeable cartridges which are arranged alongside one another and open into a mixer. To ensure that the mixing quality is not adversely affected by advancing speeds that differ depending on viscosity and friction characteristics, the advancing speed is kept at a predetermined constant value, particularly in order to obtain a constant mixing time.

EP 0 087 029 A1 relates to a device for mixing dental materials. The speed of plungers for pressing out components of the material can be controlled with pre-selected different constant speeds.

SUMMARY OF THE INVENTION

The present invention is preferably directed to a dispenser of the type sold by 3M ESPE under the trade name Pentamix™ and as also described above. Such a dispenser preferably comprises at least a first and a second compartment for a first reservoir and a second reservoir, respectively, the first and the second reservoirs containing a first and a second component for the dental material, respectively. It further preferably comprises a first and a second plunger driven by a first drive for advancing the first and the second components from the first and the second reservoirs, respectively. Moreover, a dynamic mixer driven by a second drive for automatically mixing the first and second components to form the dental material from the first and second components is provided. Such a dispenser further preferably has a dispensing portion or mixing tip for dispensing the mixed dental material.

Preferably, the mixer comprises a mixing chamber with inlets on one end for receiving the initial components, and an outlet at the opposite end for dispensing the mixture. Preferably a motor driven (dynamic) mixing element, for example a mixing rotor having mixing paddles, is accommodated in the mixing chamber. While the material, advanced by the plungers, passes through the mixing chamber from the inlets to the outlet it is mixed, preferably by shearing it transverse to its direction of flow by the mixing element. That is, the material preferably passes the mixing chamber in a direction of the rotation axis of the mixing rotor while it is sheared by the mixing paddles of the rotating mixing rotor. Because the material components once brought together may react chemically with each other, such a mixer is preferably disposable and the amount of material left in the mixing chamber is disposed with the mixer.

Preferably, the mixing element provided in said mixing chamber is driven by the second drive. Such an arrangement is described in the EP patent application with the application number 04 02 2595, the disclosure of which is incorporated by reference herein.

The present invention is more particularly directed to a dispenser or method adapted for advancing and mixing at least one dental material, comprising at least one drive which is operated on a predetermined, non-uniform drive speed profile. Preferably an advancing speed profile is provided for advancing the components and/or a mixing speed profile is provided for mixing the components, and either profile may be a "drive speed profile" as that term is used herein. More preferably both profiles are provided.

For simplicity the "non-uniform drive speed profiles" are also referred to simply as "speed profiles".

The term "speed" can embrace the desired or actual speed of one actuator or more actuators driven by the drive, such as the linear or translational speed of the plungers driven by the first drive. Alternatively, the term "speed" of the drive can embrace the desired or actual revolutions per time (generally measured in revolutions per minute, or RPM) of a drive or of a rotationally driven actuator. That is preferably the revolutions per time of the mixer driven by the second drive.

Preferably, a user fills a tray with dental impression material with such a dispenser or a method in accordance with the present invention. When a user activates the device for dispensing of the dental material, e.g. by pressing a button at the device, a cycle comprising a start-up phase, a main phase and an optional end phase is started as described in the following. The dispenser initiates the start up (or first or initial) phase and actuates the first drive for advancing the first and second components from the first and second reservoirs towards the mixer, and at the same time the second drive drives the dynamic mixer in order to ensure a proper mixing of the two or more components within the mixer before they are dispensed. All phases encompass operating both drives or at least one drive over a time period in which the speed for the other drive was zero based on the related non-uniform drive speed profile.

Because it takes some time to initially fill the volume of the mixing chamber with the dental material, the mixture is generally dispensed with a certain delay after the user has started the cycle. The start-up phase generally covers at least the time required to completely fill the mixer. The start-up phase further covers the transient phase of the mixing process, which is generally a time from a state the material components initially enter the mixing chamber until continuously homogeneously mixed material is formed by the mixer. The transient phase can be a part of the time needed to fill the mixer or a longer time. In the first case all of the dispensed material can be used, while in the latter case an initial amount of the dispensed paste may be poorly mixed and should be discarded.

After the start-up phase, the dispenser enters the main (or steady state) phase, in which the dispenser preferably dispenses homogeneously mixed dental material, e.g. into a tray for a dental impression material.

The dispenser will typically terminate the main phase and may enter an end phase when the device is stopped by the user. To stop the main phase, for example when the tray is sufficiently filled with material, the user may either release a button that has been held down to activate the device, or press a button for a second time. The device may also stop automatically when the reservoirs are empty, i.e. it may be automatically detected when the plungers cannot move any further and the device may be controlled accordingly, or after a predetermined time. In each case, the dispensing of dental material may stop immediately or with a short delay, and the dispenser may continue with an end phase as further described below.

The cycle preferably includes at least two of the start up phase, the main phase, and the end phase, and more preferably all three of them. There may be other phases in the cycle as well.

The predetermined non-uniform drive speed profile that is provided in accordance with the invention is intended to represent the speed over time of a drive during a cycle. However, the length or duration of a cycle, preferably the length of the main phase, in accordance with the invention, can change. The speed profile can moreover be set or formed by an algorithm as further described below.

The term "predetermined" is intended to exclude an embodiment with a speed profile which is just a result of a starting phase of a motor or a controlling interaction by a user during a cycle.

The term "non-uniform" is intended to embrace a speed which is essentially not constant over the cycle. A "non-uniform" speed profile may include a repetitive profile, meaning a profile consisting of two or more repetitions of a non-uniform profile segment.

Preferably, each drive is controlled in an open-loop manner. Each or one of the drives can also be controlled in a closed-loop manner, meaning that the actual drive speed is measured, and the measured values are used to adjust and control the motor.

There are preferably basically two kinds of speed profiles. The preferred first kind of speed profile is stored in memory and executed by the device. The preferred second kind of speed profile may be based on an algorithm that is in turn based on one or more variables. When the variables (e.g. capacity of reservoirs, remaining material contained in reservoirs, strength and/or size of motors, material properties, and/or variable parameters, such as time used for the main phase, ambient and/or component temperature) are input or are determined by the device, they are fed into the algorithm and the algorithm determines the speed profile, which may then be stored in a memory and executed by the device. This can be done either initially when a cycle has been started or during the cycle with an accordingly executed remaining speed profile. In such a case preferably the end phase or the phase(s) after the main phase may vary depending on the time used for the main phase.

To cause the drive(s) to follow a predetermined, non-uniform drive speed profile the invention preferably provides a memory or data storage device for storing the non-uniform drive speed profile, and a drive controller for controlling the drive according to the speed profile. Preferably the drive controller comprises the data storage device, such as a computer memory or any known data storage system.

Although the drive controller is preferably physically integrated into the dispenser, the data storage device can be a separate component which can be attached, introduced or connected to the dispenser or which communicates in any remote controlled manner, such as via RFID or wireless technology. Such a separate data storage component may have one or more speed profiles stored therein which can be accessed by the drive controller, so that a user can customize the dispenser differently with different data storage devices. Alternatively the drive controller and the storage may be integrated into the dispenser.

Such a drive controller is preferably an electronic unit comprising the data storage device, a CPU and/or logic components and other necessary electrical/electronic components.

The drive controller and the preferably integrated storage form a functional unit, also in case the drive controller and the storage are separable components. Therefore, features or functions of the storage may be further referred to as features or functions of the drive controller. The drive controller and/or the storage may comprise further electrical/electronic components or circuitry. With regard to the present invention the electrical/electronic components may not have to be located at any place in or at the device, moreover the electrical/electronic components are not necessarily located close to each other.

The drive controller may be pre-programmable by a user who can compose specific non-uniform drive speed profiles according to his or her needs.

The drive controller can alternatively and more preferably comprise a database with at least one speed profile or a plurality of speed profiles for different kinds or classes of materials. Some such materials and classes of materials are mentioned below. The database may preferably comprise at least one set of advancing speed profiles, and corresponding mixing speed profiles. The drive controller may control both the advancing and mixing drives, or a drive controller may be provided for each drive. In the latter case it is preferred that the controllers are coordinated to control both drives in parallel.

Preferably the dispenser according to the present invention comprises at least one drive for advancing and/or mixing the dental material. The drive is preferably an electric motor being controlled by at least one of voltage, pulse width, current, and frequency. In such an embodiment the drive controller is adapted to control at least one of these parameters, preferably in an open-loop manner. The motor may be a DC motor or an AC motor, DC being preferred.

A dispenser in accordance with the present invention preferably has a first drive for advancing the dental material, and a second drive for mixing the dental material. Preferably these drives are adapted to be independently operated. Preferably the first drive is operated based on the predetermined (linear or translational) advancing speed profile, to advance the material, and further preferably the second drive is operated based on the predetermined (rotational) mixing speed profile, to mix the material.

In a further preferred embodiment, both the first and the second drives each are operated based on predetermined speed profiles, to advance and mix the material in a predetermined manner, respectively. In a further preferred embodiment the speed profiles for advancing and mixing are adapted to one another to optimize their cooperation. That is, the advancing speed profile and the mixing speed profile are designed to complement each other, and accordingly to optimize one or more characteristics of the mixed material, such as setting time. In a further preferred embodiment, the speed profiles for advancing and mixing are proportional to each other, meaning that one speed profile multiplied or divided by a constant factor results in the other speed profile. The factor may be 1 if the speed profiles are identical as well as 0 if appropriate, for example if the mixing speed profile is 0.

In accordance with the present invention, two or more speed profiles may be provided which each is adapted for use with a specific material or class of materials or components thereof.

In a further preferred embodiment, the dispenser according to the present invention further comprises a sensor for identifying the dental material to be advanced and mixed, and/or the components thereof. In this case the controller is preferably adapted to select at least one of the advancing speed profiles and mixing speed profiles stored in the data storage device, according to the dental material or component(s) identified by the sensor. In the latter case the sensor may comprise components selected from among a switch, a plurality of switches, a bar code reader, a magnetic code reader, a electronic contact reader, a radio frequency reader and an optical reader.

In order to provide a detectable signal to the sensor, an identification medium may be provided at a reservoir, cartridge, or package for detecting elements which bear information for identifying a predetermined, non-uniform drive speed profile for a respective dental material to be dispensed. Alternatively or additionally a storage medium (e.g. an RFID tag, any kind of memory card, tag or medium, such as a flash memory card) comprising at least one predetermined, non-uniform drive speed profile for the respective dental material or group or class of material to be dispensed or components thereof may be provided. Such a storage medium may be delivered by a material supplier together with the material to be dispensed. In this way the device can be kept updated with regard to the non-uniform drive speed profiles, for example in case new materials are provided that may be processed in the device on specific speed profiles that are provided on the storage medium. A storage medium as mentioned may be a medium used in place of an existing data storage device of the drive controller. Alternatively such a storage medium may be used to transfer the non-uniform drive speed profiles to an existing storage of the drive controller, and finally it may be used in addition to an existing storage.

The present invention is also directed to such packages, reservoirs or cartridges with more than one reservoir with an identification medium or a storage medium as described above.

Preferably a non-uniform drive speed profile according to the present invention comprises a section for operating the first drive at a negative speed, meaning to provide reverse movement of the plunger(s). This is particularly useful at or close to the end of a cycle, in order to relieve the pressure built up by the plunger(s) in the materials reservoir(s) of the dispenser during use, or even to retract mixed material from a dispensing or mixing tip and to prevent material from flowing out or being wasted after a dispensing cycle has finished. In the absence of such a feature, the residual pressure resulting from elastic relaxation of the material compartments when the device is turned off can cause such material flowing and waste.

A non-uniform drive speed profile alternatively or preferably additionally comprises at least two phases for driving the first drive and/or the second drive during a main phase with a steady state speed, and during a pre-main phase with a pre-steady state speed which is faster than the steady state speed.

More preferably the method or device according to the invention has a speed profile for the advancing speed and/or the mixing speed with at least two of the following phases and at least one of the respective sections:

A start up phase, comprising:
a first section with an increasing speed;
a second section with a load peak speed; and
a third section with a decreasing speed;
A main phase, comprising a fourth section with a constant speed;
An end phase, comprising:
a fifth section with a decreasing speed;
a sixth section with a negative speed; and/or
a seventh section with a speed increasing from the negative speed back toward or to zero.

The phases and sections have been named and numbered for a better understanding, but the names and the numbers are not intended to provide any preference or order of steps. The speed profile may also have more or less phases and/or sections than those that are mentioned. In a more preferred embodiment at least the fifth to the seventh sections and in another preferred embodiment at least the second to the fifth sections are present, in the order as shown above.

When a user initiates a cycle, the speed profile will preferably begin with the start-up phase having a relatively high speed, in order to particularly advance the components to and into the mixer and to enable a proper mixing of the material or components at the beginning. This is true particularly when the mixer is not entirely filled. The start-up phase having relatively high speeds preferably continues as long as the user does not deactivate the main phase of the dispenser, e.g. by releasing an activation button or by preferably pressing a control button a second time. When no further material is needed, and for example the user releases the activation or control button, then the speed profile for the advancing speed preferably continues with a decreasing speed, and at or near the end of the cycle even with a negative speed. In any case, at least the essential length of the main phase is preferably controlled by the user.

The remaining phase(s) and section(s) of the speed profile, is or are preferably not influenced by the user. Optionally the sections following the main phase depend on the duration of the main phase. This can be advantageous for speed profiles in which the first drive is driven with a negative speed to relieve pressure that has built up in the material reservoirs, because different durations of the main phase may result in different pressures that can be diminished.

A preferred dispenser according to the present invention comprises at least a first and a second compartment for a first reservoir and a second reservoir, respectively, the first and the second reservoirs containing a first and a second component for the dental material, respectively. Moreover, a first and a second plunger are provided and driven by the first drive for advancing the first and the second components from the first and the second reservoirs, respectively. Furthermore, the dispenser has a dynamic mixer driven by a second drive for automatically mixing the first and second components to form the dental material. Preferably a dispensing portion for dispensing the mixed dental material is also provided.

These concepts are preferably realized with the Pentamix™ dispenser described above and more preferably in a dispenser as further described in the EP application with the application number EP 05005367, the disclosure of which is herein incorporated by reference.

With the above described structure or method, dispensing rates of at least 120 $cm^3$/min, preferably of at least 125 $cm^3$/min, more preferably of at least 130 $cm^3$/min, more preferably of at least 140 $cm^3$/min, more preferably of at least 150 $cm^3$/min can be obtained. Such dispensing rates are provided by the present invention because the parameters are selected to optimize the performance of the device and the material. For example, the parameters include also advancing at high speed but mixing at low speed to reduce the heat development to the material, which influences the properties of the mixture after it has been dispensed. In contrast, prior art devices are generally designed to provide good mixing quality or maximum drive performance only, without regarding other secondary effects on the material properties.

The present invention also embraces a kit with the above described dispenser and at least one cartridge.

The present invention is directed to a device, a method, an identification medium, a storage medium, a reservoir, a cartridge, and/or a kit, all of which are particularly adapted for dispensing dental impression material, more particularly with a base component and a catalyst component.

It is a preferred advantage of the present invention to provide a dispenser and method for controlling the dispensing or expelling of flowable dental material or components thereof in a manner which can be more efficient and reliable, and produce mixed dental materials of a high quality.

A further preferred advantage of the present invention is to provide a dispenser and method for controlling the dispensing of flowable dental material or components thereof in a manner that reduces the transient phase of the mixing process in the mixer. Because at the beginning of the mixing procedure the mixer is only partially filled with material, the quality of the mixed material is worse than in the main phase. Therefore it is common practice to discard the initial amount of material dispensed from a device of the prior art until the steady state is reached. The device of the present invention, because of the predetermined drive speed profiles, provides better mixing quality from the beginning. This saves time on one hand, because less material has to be discarded before the quality of the mixed material is sufficient. On the other hand it saves costs for the material, which is otherwise discarded.

Because the speed profiles are predetermined, and not as in the prior art user defined or adjusted to the material properties only, the device can preferably provide reliable and accurate speed parameters with respect to the material properties, the properties of the device and the properties of the mixer used with a specific material. These parameters are more accurately determined by the device manufacturer and the material supplier than by the user, and thus improved material performance can be expected. Specific advancing drive speed profiles, and mixing speed profiles, may be determined by people of skill in the art based on the properties of the materials to be used.

With regard to specific mixing speed profiles, such a speed profile may comprise a high mixing speed at the beginning of the mixing process until the mixer has been filled, and a lower speed for the main phase, to ensure homogeneous mixing while limiting the heat generated in the material by the mixing process. Heating the material during mixing can cause the material to cure more quickly than is desirable, thus reducing working time, so this predetermined non-uniform mixing speed profile is believed to be beneficial.

In another example, an advancing speed profile may comprise a rather low advancing speed at the beginning in order to advance the individual components of the material synchronously. This may be required for material components having different flow characteristics relative to each other. The effect of non-synchronous advancement of such materials may be caused mainly because different flow characteristics of the material components cause different forces on the corresponding plungers. Because the construction of device generally provides limited stiffness for guiding the plungers, slight tilting of the plungers may occur when loading the plungers with different forces. Therefore a dispenser and material-specific speed profile might be required.

There may be other materials which in combination with the use of the device and a mixer require certain speed profiles to be mixed and dispensed at a high quality and the maximum possible speed. For example, a speed profile for the mixer and/or the plunger speed can comprise decreasing speed over time or increasing speed over time, or both sequentially.

The present invention preferably provides the ability to dispense a variety of materials at a high mixing quality and at the maximum possible speed over the whole mixing cycle. Generally the mixing quality depends on the shear strain applied to the material in the mixer, which generally is provided by the rotation of mixing paddles driven at the mixing drive speed. Because the material to be mixed is advanced continuously through the mixer, the material will be exposed to a certain number of revolutions of the rotary mixing paddles, which in the absence of the present invention may or may not be sufficient to provide a good mixing quality. Therefore the mixing quality depends on both the mixing drive speed and the advancing drive speed, which are implemented in the manner described herein. Conventional user-adjustable devices generally would be adjusted primarily to get optimum mixing quality. In contrast, the invention provides the advantage of driving one of the advancing or mixing speed always or both at its possible maximum for a variety of materials, because the optimum speed parameters, which are generally non-uniform over the dispensing process, are predetermined and stored in the device.

Still another advantage of the present invention is the preferred predetermined low mixer speed during the time when a new mixer is being connected with the drive shaft, prior to the initiation of a dispensing cycle. More preferably, the device of the invention comprises a drive shaft which is movable along its longitudinal axis against a spring. This is useful to ensure that the mixer drive shaft connects to a new mixer properly after it has been placed on the drive shaft. During the operation of the mixer at a very low speed, the drive shaft will be moved axially back to its desired position so as to securely connect with the mixer. To securely connect the drive shaft with the mixer the drive shaft is preferably operated at a speed below the mixing speed, preferably a speed of above 0 and below +/−100 rpm and more preferably between +/−5 and +/−50 rpm. Axial movement would otherwise be hindered because during operation at a high speed the drive shaft transmits a high torque resulting in a high friction between the drive shaft and the mixer.

The present invention has the further preferred advantage that it is able to provide a customized method for controlling the advancement of dental material and/or a customized method for mixing at least two dental components. The combination of the method for advancing and the method for mixing are particularly well adapted to be more efficient in terms of reliability, time and/or condition of the dental material that is dispensed. This is particularly valuable in view of the increasing variety of dental materials or components thereof, each with different parameters such as curing times, flowing and mixing conditions, pre-reaction viscosity of the two components, reaction speed of the components, the thermodynamics of the chemical reaction, viscosity build-up profile during the extrusion and final flow characteristics of the mixed dental material upon exiting the device. Thus, the present invention makes it possible to specifically customize or individualize the advancing and mixing process for this variety of materials and components thereof.

Moreover, it is an advantage of the present invention that it saves a dentist time by dispensing the bulk of the material in the main phase, between the start-up and end phase, under highest possible speed depending on the material parameters of the differing dental materials. This is preferably done without mixing the material at the highest possible speed, which can as noted previously cause increased temperatures that in turn result in less curing time and working time for the materials.

Another preferred advantage is provided by the possibility of mixing highly viscous materials at a lower mixing speed, but using a high advancing speed. Therefore it is possible to mix the material at a rather low power, which permits the device to use a relatively small motor.

To achieve a homogeneous mixture, the mixing speed can be initially, during the start-up phase, driven at a high speed which a small motor provides, because the mixing chamber is not yet filled with material. Lower mixing speeds can then be used when the mixing chamber has filled with material, which also does not require a large, powerful motor.

It is a further preferred advantage of the present invention to prevent the impression material from flowing out of a dispensing device in an uncontrolled manner after dispenser has been shut off (which makes a mess and wastes impression material) by running the first motor in reverse at or near the end of the cycle.

Moreover, the invention provides the preferred advantage to have the option to start at the beginning with higher mixing speeds to ensure that even an initial volume of material delivered is uniformly mixed.

BRIEF DESCRIPTION OF THE FIGURES

The following figures are intended to exemplify preferred embodiments in accordance with the present invention and are not intended to limit the scope of protection of the claims in any manner.

FIG. 1b is a schematic illustration of an arrangement and interaction of members of the dispenser according to FIG. 1a;

DETAILED DESCRIPTION OF THE FIGURES

Figure 1A:
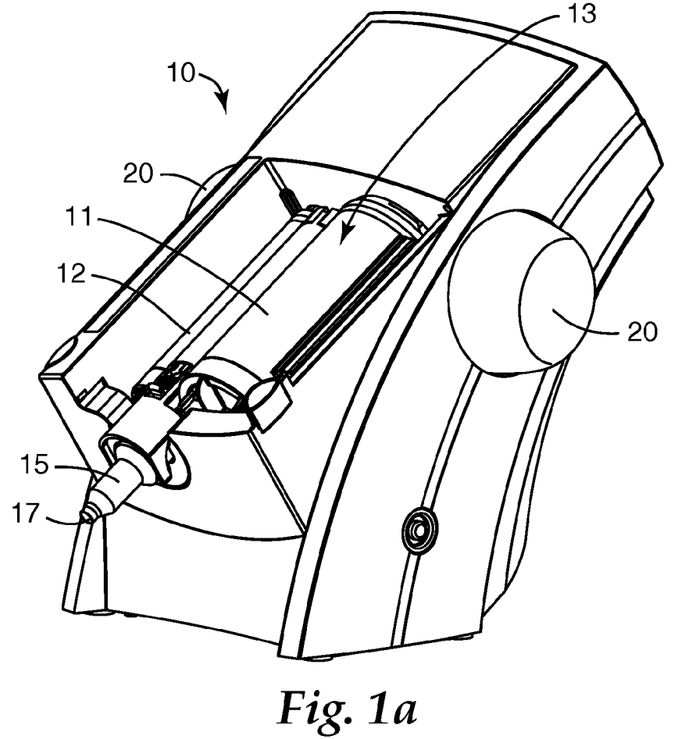
FIG. 1a is a perspective view of an embodiment of a dispenser for use in accordance with the present invention.

FIG. 1 shows an example of a dispenser 10 which preferably comprises two adjacent parallel compartments 11, 12 suitable for containing components for the dental material in reservoirs. A first drive is provided for advancing two plungers (not shown), which serve as force transmitting members and are movably disposed within the respective compartments 11, 12 for displacing the components or substances contained in the compartments 11, 12 in a forward direction. The first drive preferably includes an electrical motor, which is coupled to the plungers in any suitable manner for driving the plungers. Preferably the first motor and the plungers are coupled via a so-called push-pull chain, as described in co-pending EP application with the EP application number 05 00 5367 which is incorporated by reference herein.

A mixer 15 is in fluid communication with outlets at the front ends of the compartments 11, 12 (not shown). The plungers are preferably rigidly interconnected at their back ends by a transverse member (not shown) for ensuring that the plungers are driven simultaneously into the compartments, but the plungers could be independently driven by a single drive or by plural drives. Each plunger preferably comprises a plunger head and plunger rod. Plungers may also be referred to as pistons.

In operation, a cartridge 13 having the compartments 11, 12, each containing a pre-packaged component or substance in a reservoir, such components provided in a foil bag, is placed into the dispenser 10. The plungers are designed such that their plunger heads may abut the back ends of the packaged components or substances. The plunger heads, although not further illustrated, are dimensioned to fit within the respective compartment 11, 12 but preferably have a larger diameter than the plunger rods. The plungers are rigid in order to ensure that sufficient thrust force is applied in the longitudinal axial direction. As plungers are moved forward within compartments 11, 12, the respective reservoirs are opened. The plungers are slowly advanced into respective compartments 11, 12 so as to urge the two components into the mixer 15. The components or substances are mixed in the mixer 15 to form a ready-to-use dental material, which is forced out of a dispensing portion such as mixing tip 17 in a known manner.

A second drive (not shown), preferably an electrical motor, drives a mixing shaft in the mixer 15, preferably in a manner as described above.

Rotatable knobs 20 are shown, which are arranged preferably at both sides of the dispenser 10 and which are coupled with the drives and/or plungers and/or other suitable members of the drive and which allow for manual movement of the plungers. For example the plungers can be manually advanced forward toward or into the cartridge (which is the direction toward the mixer), when a cartridge 13 has been newly inserted into dispenser 10, or they can be manually moved backwards (which is the direction away from the mixer) to disengage the plungers from the cartridge and allow a used cartridge 13 to be replaced.

Figure 1B:
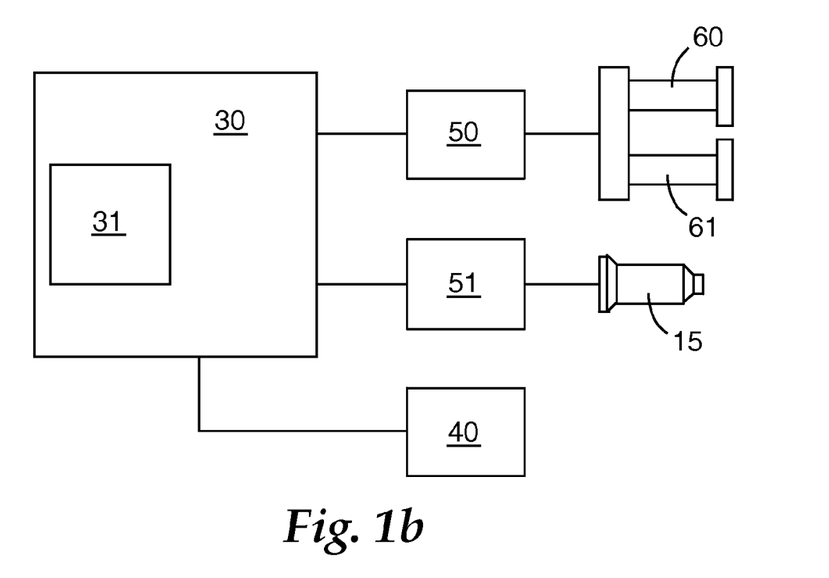

FIG. 1b illustrates a preferred embodiment of a drive controller 30 comprising a data storage device 31, as well as other components already mentioned above. A sensor 40 is preferably arranged to determine from the material package or the like the class of material or other parameters described above. Preferably an indicator is provided on cartridge 13 shown in FIG. 1a, and the sensor 40 is able to read this indicator. In FIG. 1b, the drive controller 30 after having received information from the sensor 40 then selects the appropriate speed profile corresponding to the detected material or class of materials from the data storage device 31, and drives the two drives 50, 51 accordingly when a dispensing cycle is initiated. The first drive 50 drives the plungers 60, 61 linearly with an appropriate gear box, or preferably by a push-pull chain arrangement. The second drive 51 drives the mixer 15 via a rotating mixing shaft contained therein. The information that the sensor of the device reads from an indicator/tag/barcode can either include the actual drive profile(s), or just a reference number (e.g., material class) or other information that enables the device to search an existing database for a corresponding entry, and then use the profile(s) stored under that entry to run the drive(s). The information can also comprise the speed profile (e.g., a material specific speed profile) which is combined with a speed profile already stored in the drive controller.

Figure 2A:
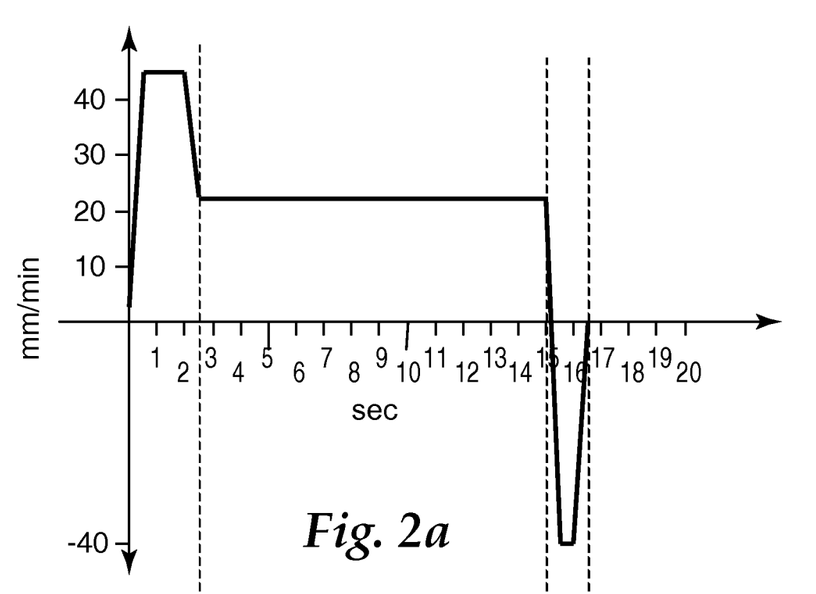
FIG. 2a shows a preferred non-uniform drive speed profile for an advancing speed for a specific first class of materials to be dispensed.
Figure 2B:
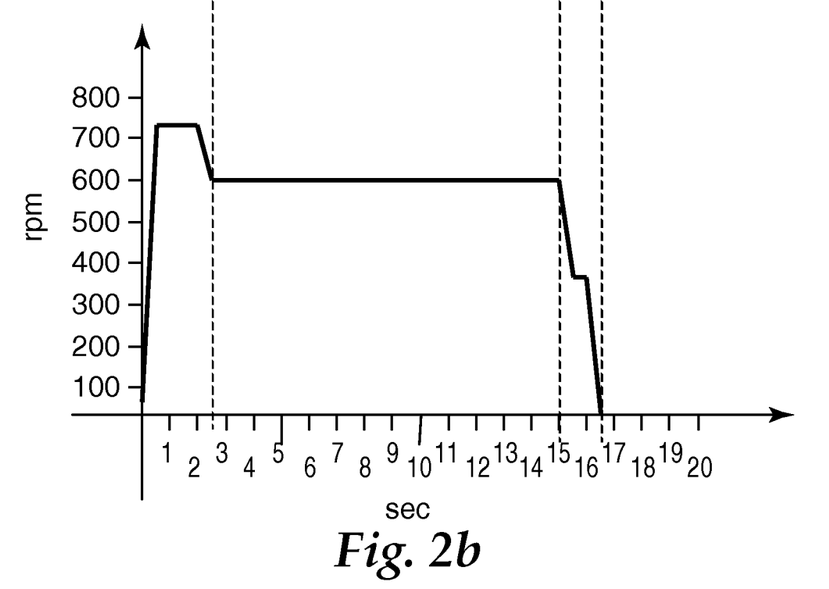
FIG. 2b shows a preferred non-uniform drive speed profile for a mixing speed for the specific first class of materials.
Figure 3A:
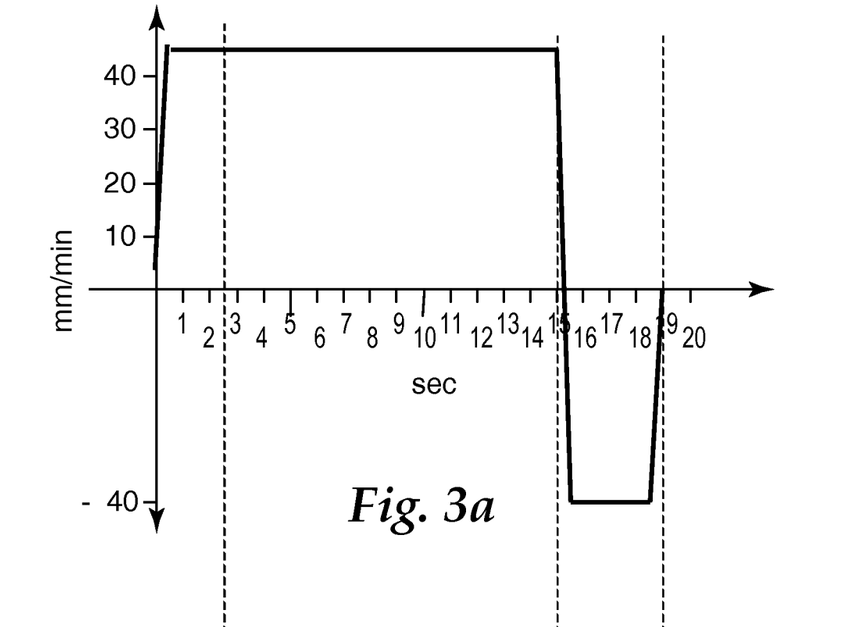
FIG. 3a shows a preferred non-uniform drive speed profile for an advancing speed for a specific second class of materials to be dispensed.
Figure 3B:
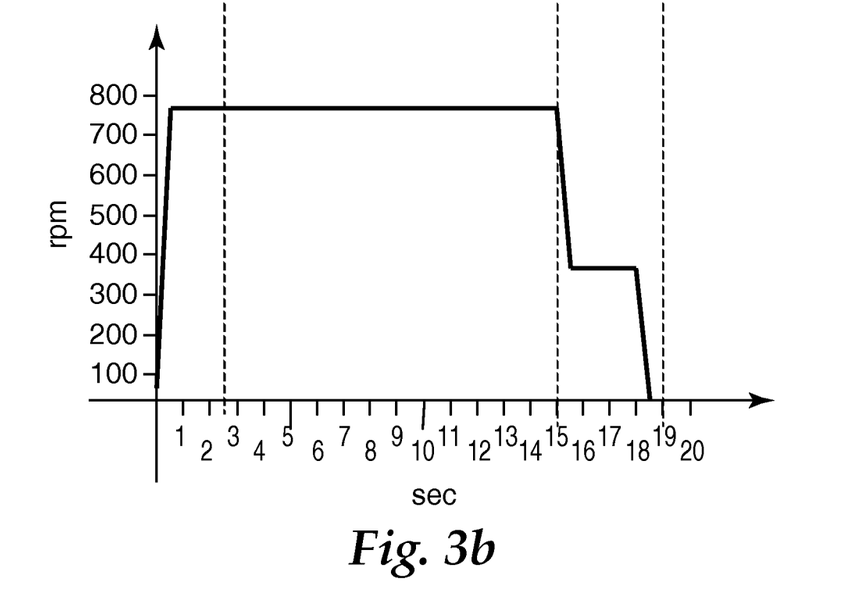
FIG. 3b shows a preferred non-uniform drive speed profile for a mixing speed for the specific second class of materials.
Figure 4A:
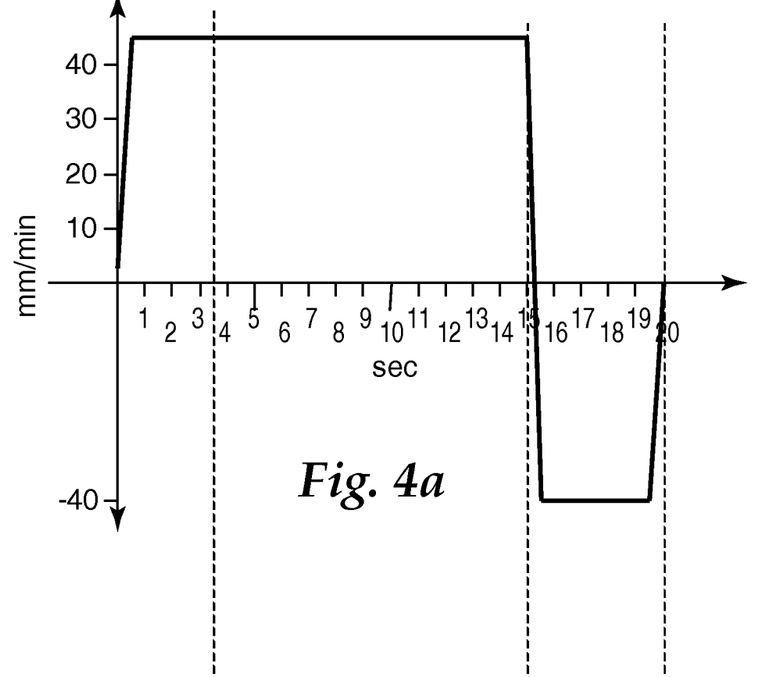
FIG. 4a shows a preferred non-uniform drive speed profile for an advancing speed for a specific third class of materials to be dispensed.
Figure 4B:
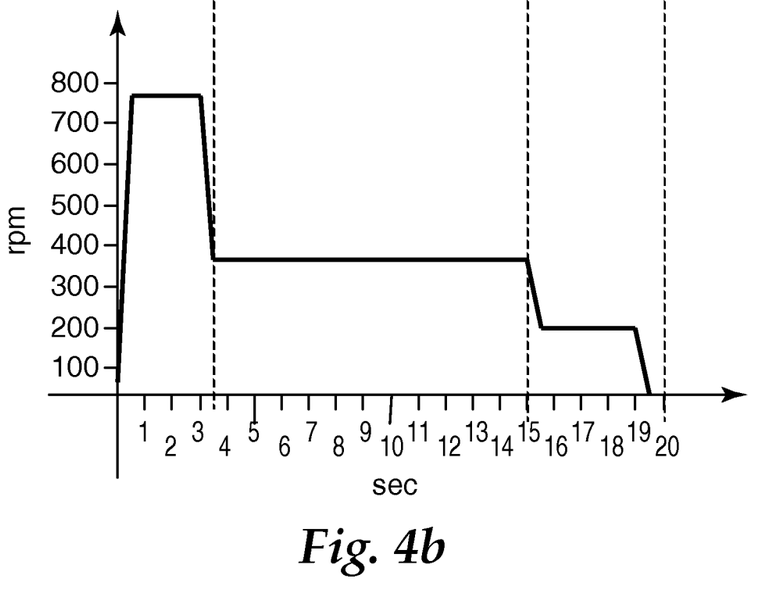
FIG. 4b shows a preferred non-uniform drive speed profile for a mixing speed for the specific third class of materials.

FIGS. 2-4 show cycles with different speed profiles for the first and the second drives and for different materials that are mainly distinguished by their flow characteristics. FIGS. 2a, 3a, 4a show advancing speed profiles as a function of time. FIGS. 2b, 3b, 4b show mixing speed profiles as a function of time.

In very general terms, the viscosity of the materials depends on the chemical composition and the content of fillers. Again in very general terms, the higher the content of fillers (e.g. quartz), the higher the viscosity. The higher the viscosity, the higher are the forces the drives have to provide, and the higher is also the shear rate within the material when the material is mixed in the mixer, and the more the temperature will increase within the material when the material is mixed. These factors can be taken into account when designing the drive speed profiles.

There are materials which are mixed from components having different viscosities. Depending on the viscosity and mixing ratio, the fact that the pressure builds up differently in the individual compartments at the start of the dispensing cycle as also discussed above may cause the components to reach the mixer at different times. In such a case, the initial volume of material dispensed from the mixer has a mixing ratio which differs from a desired value, and may therefore cure less perfectly or more slowly, or have other undesired properties. It should be discarded.

In order to take account of the above problems and to provide an improved dispenser and method of dispensing, the individual speed profiles as exemplified in FIGS. 2-4 are proposed. FIG. 2 show speed profiles for components or a dental material with a relatively low viscosity according to DIN 4823, material type 3. The optimized speed profile according to FIG. 3 have been found for a high viscosity material according to DIN 4823, material type 1, and the speed profile according to FIG. 4 have been found for a putty viscosity material according to DIN 4823, material type 0.

All FIGS. 2-4 show generally three phases, although there may be more or less such phases (the dividing line between the sections is generally the change of gradient/slope of the curve). These phases are separated by dotted lines in FIGS. 2-4 and contain a first start up phase, a main phase, and an end phase. These phase designations are exemplary, and the speed profiles shown could be divided into more or fewer phases, or at different points in time.

In FIGS. 2a, 2b the start up phase comprises a first section with a relatively quickly increasing speed, a second section with a relatively high load peak speed, and a third section with a decreasing speed. This reflects the fact that in case of FIG. 2a (relatively low viscosity) a sufficient pressure can be quickly built up initially in the compartments or reservoirs with relatively small drives, which then quickly forces the material to the mixer. Due to this rather dynamic behavior of the components or the material, the mixer is initially turned very quickly in order to provide an appropriate initial mixing, particularly when the mixer is not entirely filled as described above. This is shown in FIG. 2b. The material is sensitive to temperature increase due to the mixing. Thus, the advancing speed and the mixing speed is reduced to a steady state speed in the main phase as is apparent from FIGS. 2a and 2b, respectively.

In the end phase, the advancing speed in FIG. 2a shows a fifth section with a decreasing speed, a sixth section with a negative speed, and a seventh section with a speed increasing from the negative speed toward or to zero. The plungers are refracted (in a direction away from the mixer or out of the compartments) to relieve the pressure within the components and to reduce the pressure toward or to zero in order to prevent a further flow of material out of the mixing tip. FIG. 2b shows a respective reduction in mixing speed. The mixer typically does not apply a negative (reversed) mixing direction, because the mixer is generally not able to advance or reverse the material contained therein, and because reversing the mixing direction still results in mixing. The mixing speed is essentially an absolute value, However, the invention allows for providing a mixing speed in two directions (for example for achieving improved mixing quality or for driving a mixer providing for different mixing effects in different directions).

In FIG. 3a, the advancing speed in the start up phase is brought up to the steady state speed in the main phase. Due to the fact that the viscosity of the components is higher than in the case illustrated in FIG. 2, the force provided by the drives or motors is relatively high to build up a sufficient force and then to appropriately advance the components into the mixer. The end phase has a speed profile segment similar to that shown in FIG. 2a, but is longer in time since in FIG. 3a the higher viscosity components need more time and space to relieve the pressure when the plungers retract. The same holds true for the case shown in FIG. 4a.

As is shown in FIGS. 3b and 4b the mixer driven by the second drive may stop slightly earlier than the plungers driven by the first drive. Even when no components are advanced to the mixer, additional time is needed to reduce the pressure within the compartments toward or to zero, and to prevent further unintended dispensing from happening after the device stops.

Figure 5A:
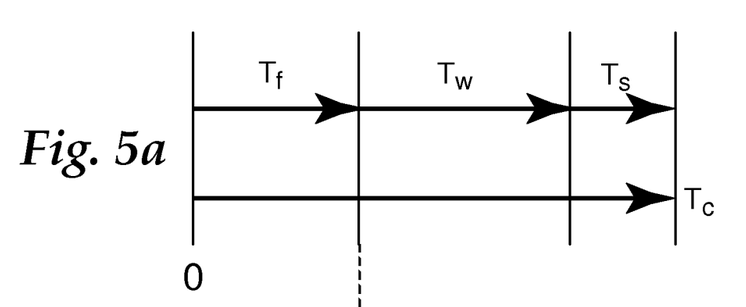
FIGS. 5a-c show tray filling, working and solidifying times according to the prior art, with an unduly reduced setting time, and in accordance with the present invention, respectively.
Figure 5B:
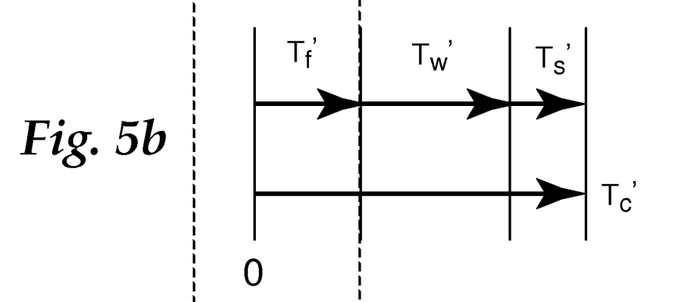
Figure 5C:
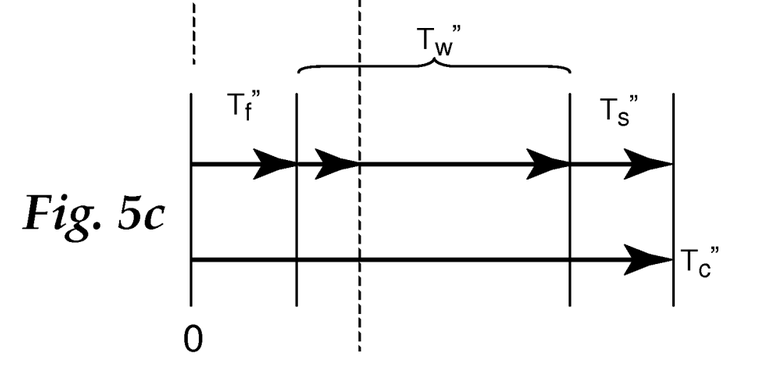

FIGS. 5a-c shows the three time periods that when added together are equal to the total curing time, Tc. First, there is the time needed to mix the components and dispense them into a dental tray, which is shown as $T_f$. Second, there is the working time needed to position the filled tray inside the patient's mouth with the impression material surrounding the teeth, which is shown as $T_w$. Third, there is the solidifying time during which the impression material should not be moved relative to the teeth, so that the impression material produce an accurate replica of the teeth, shown as $T_s$. These times, for prior art materials and dispensing devices, as shown in FIG. 5a.

FIG. 5b shows the behavior of a material which is sensitive to temperature increases developed during mixing, due to shearing the material within the mixer. If a user simply increases the advancing speed and the mixing speed in an effort to dispense the material more quickly, the increased temperature of the impression material results in faster curing. On one hand the time to fill a tray can be reduced to a shorter time $T_f'$ which would generally be desirable. On the other hand, because the curing time as illustrated as time $T_c'$ is shortened, the working time and solidifying time and shown as $T_w'$ and $T_s'$ may be dramatically reduced. This gives the user much less, and possibly too little, time to appropriately place the tray filled with impression material into a patient's mouth. In other words, increasing the advancing speeds and the mixing speeds, in an attempt to increase the speed of the overall impression process, tends to lead to unsatisfactory results. This recognition forms part of the present invention.

The present invention is able to provide optimum processing conditions for different components or classes of materials, by driving the mixing speed and/or the advancing speed using a predetermined non-uniform drive speed profile. Depending on the dental material and other parameters, that speed profile may include different phases and sections for advancing, mixing and dispensing the components or material.

FIG. 5c shows that with the dispenser and method according to the present invention, the tray filling time can be reduced to a shorter time $T_f''$ but generally without causing the material to cure faster because the mixing speed is minimized and the advancing speed is maximized by driving both on non-uniform drive speed profiles according to the invention. Thus, the temperature developed during mixing is approximately equal to the situation illustrated in FIG. 5a, so that also the curing time $T_c''$ is generally not shortened as in FIG. 5b but equal to $T_C$ ($T_c''=T_c$). This also allows the assumption that the solidifying time $T_s''$ generally is not shortened ($T_s''=T_s$). Overall, the shortened filling time $T_f''$ will directly result in an increased working time $T_w''$ because $T_f''$ and $T_w''$ add. to a period generally equal to the situation in FIG. 5, and therefore a decrease of one results in an increase of the other. In this way the working time for the professional can be increased without chemically changing the material, which is a considerable advantage.

EXAMPLES

Examples of materials which can be dispensed, such as the ones provided by 3M ESPE, are the impression materials "Position™ Penta™", "Position Penta™ Quick", "Impregum™ Penta™ Soft", "Impregum™ Penta™ H DuoSoft", "Impregum™ Penta™ L DuoSoft", "Impregum™ Penta™", "Permadyne™ Penta™ H", "Permadyne™ Penta™ L", "Dimension™ Penta™ H", "Dimension™ Penta™ L", "Dimension™ Penta™ H Quick", and "Ramitec™ Penta™", each filled in respective catalyst and base reservoirs.

Areas of material which were not mixed homogeneously were quite clearly identified by strands visible at the cutting surface because of their different colour relative to each other, or relative to the areas they occur in.

Comparative Example

A device for mixing and dispensing two-component dental impression materials available commercially as Pentamix™ 2 Dispenser from 3M ESPE was used in the following manner:

The device was loaded with a two-component dental impression putty material supplied in two foil bags as commercially available as Express™ Penta™ from 3M ESPE. The foil bags, one containing the base paste and a second containing the catalyst, were inserted into a dual cartridge as also commercially available for the Pentamix™ 2 Dispenser, and the cartridge was loaded into the device.

The impression material was mixed and dispensed by conventional use (which can be taken from the instructions for use available with the device) of the device into a dental tray as commonly used in the dentistry for making models of teeth. The tray had a size for containing 50 g of the mentioned material.

The advance speed was uniform and the mixing speed are provided by one motor at a fixed ratio relative to each other. The advance speed was uniform at approximately 22.5 mm/minute which is the speed ordinarily provided by the device. The mixing speed, also the one ordinarily provided by the device, was uniform at approximately 360 rpm. Both speeds are nominal speeds, meaning that the actual speeds may have been slightly different (probably lower) from the mentioned speeds because of the load to the drive of the device resulting from the energy needed to advance and mix the materials.

The device was started and stopped manually. The total time to fill the tray with 50 g impression material was 37 seconds.

Example One

A device for mixing and dispensing two-component dental impression materials according to the invention having a motor for providing the advancing speed and a separate motor for providing the mixing speed was used in the following manner:

Drive speed parameters have been devised for a putty viscosity two-component dental impression material, commercially available as Express™ Penta™ from 3M ESPE as in the Comparative Example and stored in the drive controller of the mentioned device.

A cartridge with two foil bags with the mentioned material as also used for the Comparative Example and fitting with the device of the invention was additionally provided with a chip containing the information used for selecting the drive speed profiles (speed vs. time) devised for this material. The advancing speed profile and the mixing speed profile were as shown in FIGS. 4a and 4b, respectively. The device read the information off the chip on the cartridge.

The mixing and extrusion process was initiated by manually advancing the plungers close to the ends of the foil bags, and then pressing the "Start" button on the device to activate the dispensing program.

Start up phase: The device automatically began with a start-up phase lasting about 3.5 seconds. During this phase the plunger, driven by the first drive according to the invention, was advanced at a speed of 45 mm per minute to expel the impression material into the mixing tip. The second drive according to the invention, driving the mixer, was driven a rate of 750 rpm. As in the Comparative Example the mentioned speeds are nominal speeds so that the actual speed may have been slightly different (probably lower) than those mentioned. For better definition the speed of the first and second drives during their ramp-up and slow-down operations are not further described.

Main phase: The device automatically moved into a main phase lasting about 11.5 seconds where the impression material flowed through the mixing tip and directly into a tray. The mixer was driven at a speed of 370 rpm (nominal speed). During this phase the advancing speed of the plunger was still 45 mm per minute (nominal speed).

End phase: When the user released the "Start" button, the device automatically proceeded with a pre-determined end phase lasting for 5 seconds. During this phase, the first drive was driven at a negative speed (driven in the opposite direction) at −44 mm/min (nominal speed) so as to move the plunger in the reverse direction and to reduce the pressure inside the foil bag and the mixer. The mixer turned at a rate of 190 rpm (nominal speed).

The device stopped automatically after the end of end phase after a total of about 19 seconds, which was sufficient to fill the tray with 50 g of the material. Thus the overall time for filling the tray was approximately ½ of the time needed in the Comparative Example. The mixing quality was evaluated separately by use of the devices and parameters as can be taken from the examples above. According to the test method described below the mixing quality of the material dispensed from the Pentamix™ 2 and the material dispensed from the device according to the invention are the same. The homogeneity of the extruded impression material was evaluated by the following method.

A strand of dental impression material having a length of approximately 10 cm and a diameter of approximately 8 mm was extruded onto a platform on a motorized stage using the device of the invention as described below, so that the resulting strand of impression material laid on the surface of the platform in a straight line. The dental material was made by mixing two components having different colours so that quality of the mixing of the two materials could be approximated by visually examining the change in colour along the length of the extruded strand. A more precise approximation of the mixing quality was done with a strand which was cut in half lengthwise.

As noted above, however, simply dispensing the material more quickly is not always advantageous, if the mixed material is not uniformly mixed or cures too quickly.

Further examples for which a device according to the invention has been used are summarized in the table below.

For comparison, the putty material used in the Examples above is also included in the table.

| Material | | Start-up phase | Main phase | End Phase |
|---|---|---|---|---|
| Example A Low viscosity impression material DIN 4823 Type 3 | mixer speed rpm | 760 | 600 | 380 |
| | plunger speed mm/min | 45 | 22.5 | −45 |
| | duration sec | 2.5 (total: 2.5) | 12.5 (total: 15) | 1.5 (total: 16.5) |
| Example B High viscosity impression material DIN 4823 Type 1 | mixer speed rpm | 770 | 770 | 390 |
| | plunger speed mm/min | 43 | 43 | −43 |
| | duration sec | 2.5 (total: 2.5) | 12.5 (total: 15) | 4 (total: 19) |
| Example C (described above) Putty viscosity material DIN 4823 Type 0 | mixer speed rpm | 750 | 370 | 190 |
| | plunger speed mm/min | 44 | 44 | −44 |
| | duration sec | 3.5 (total: 3.5) | 11.5 (total: 15) | 5 (total: 20) |

The three examples have been conducted by use of the parameters as defined in the table above. It has been proven that the invention provides for a reduction of the time to fill a dental tray. In examples B and C the time was approximately half of the time required by a standard Pentamix™ 2 Dispenser from 3M ESPE. In any of the examples A, B and C the mixer was filled twice as fast relative to the time required with a prior art dispenser mentioned. This provides for an overall shorter time to fill a tray and to quickly overcome the transient phase during filling of the mixer with material, so a steady state is reached faster. Furthermore, because the material once mixed together starts curing and therefore increasing its viscosity continuously, the invention provides that a filled tray contains material having more equal consistency between the material filled first and the material filled last relative to the prior art. Therefore the precision of the impression is improved.

Although the invention has been described in the context of one category such as in the device category, the respective features in other categories are intended to also be embraced by the present invention and description.

The present invention is intended to embrace also embodiments with combinations of features which have been described in connection with different embodiments above.

The invention claimed is:

1. A dispenser, comprising:
   (a) at least a first reservoir and a second reservoir, for containing a first and a second component for a dental material, respectively;
   (b) a first and a second plunger driven by a first drive for advancing the first and the second components from the first and the second reservoirs, respectively;
   (c) a mixer driven by a second drive for mixing the first and second components to form the dental material from the first and second components; and
   (d) a dispensing portion,
   wherein the first drive is configured to operate based on a first predetermined, non-uniform drive speed profile to first advance the first and second components from the first and second reservoirs, then, after advancing the first and second components from the first and second reservoirs, retract the first and second plungers to relieve built-up pressure within the first and the second reservoirs, and, after relieving built-up pressure within the first and the second reservoirs, stop the first and second plungers at positions more advanced than prior to the advance of the first and second components from the first and second reservoirs.

2. The dispenser according to claim 1, further comprising a drive controller for storing the first predetermined, non-uniform drive speed profile and for controlling the first drive according to the first predetermined, non-uniform drive speed profile.

3. The dispenser according to claim 1, wherein the first and second drives are independently operable.

4. The dispenser according to claim 1, wherein the second drive is operated based on a second predetermined, non-uniform drive speed profile, and the first and second predetermined, non-uniform drive speed profiles are coordinated with one another.

5. The dispenser according to claim 4, wherein the first and second predetermined, non-uniform drive speed profiles are each adapted for use with specific material or class of materials.

6. The dispenser according to claim 1, comprising a sensor for identifying the dental material to be advanced and mixed and/or components for the dental material.

7. The dispenser according to claim 6, wherein a drive controller is adapted to select the first predetermined, non-uniform drive speed profile according to the dental material identified by the sensor.

8. The dispenser according to claim 6, wherein the sensor comprises components selected from a switch, a plurality of switches, a bar code reader, a magnetic code reader, an electronic contact reader, a radio frequency reader and an optical reader.

9. The dispenser according to claim 1, wherein the advancing speed profile comprises a section for driving the first drive at a negative speed.

10. A method for operating the dispenser defined in claim 1, the method comprising:
    controlling the first drive according to the first predetermined, non-uniform drive speed profile to first advance the dental material with the first drive, then relieve built-up pressure within the first and the second reservoirs, and, after relieving built-up pressure within the first and the second reservoirs, stop the first and second plungers at positions more advanced than prior to the advance of the first and second components from the first and second reservoirs, and
    mixing the dental material with the second drive.

11. The method according to claim 10, further comprising independently operating the first and second drives.

12. The method according to claim 10, wherein the second drive is operated based on a second predetermined, non-uniform drive speed profile, to mix the material.

13. The method according to claim 12, wherein the first and second predetermined, non-uniform drive speed profiles are coordinated with one another.

14. The method according to claim 12, wherein the first and second predetermined, non-uniform drive speed profiles are each adapted for use with specific material or class of materials.

15. The method according to claim 10, further comprising driving the first drive to run at a negative speed to provide reverse advance movement in accordance with a respective section of the first predetermined, non-uniform drive speed profile.

16. The dispenser according to claim 4, wherein the second predetermined, non-uniform drive speed profile comprises a section providing the second drive to run on a low speed of approximately 5 to 50 rpm to facilitate coupling of the mixer with the second drive.

17. The method according to claim 12, wherein the second predetermined, non-uniform drive speed profile comprises a section providing the second drive to run on a low speed of approximately 5 to 50 rpm to facilitate coupling of the mixer with the second drive.

18. The dispenser according to claim 1, wherein the first predetermined, non-uniform drive speed profile is predetermined before the material is dispensed.

19. A dispenser, comprising:
(a) at least a first reservoir and a second reservoir, for containing a first and a second component for a dental material, respectively;
(b) a first and a second plunger driven by a first drive for advancing the first and the second components from the first and the second reservoirs, respectively;
(c) a mixer driven by a second drive for mixing the first and second components to form the dental material from the first and second components; and
(d) a dispensing portion,
wherein the first drive is configured to operate based on a first predetermined, non- uniform drive speed profile,
wherein the first predetermined, non-uniform drive speed profile is predetermined before the material is dispensed,
wherein the second drive is configured to operate based on a second predetermined, non- uniform drive speed profile, and the first and second predetermined, non-uniform drive speed profiles are coordinated with one another,
wherein at least one of the first and second predetermined, non-uniform drive speed profile comprises the following sections for driving at least one of the first drive and second drive:
(a) a first section with an increasing speed starting from 0;
(b) a second section with a peak speed;
(c) a third section with a decreasing speed;
(d) a fourth section with an essentially constant steady state speed;
(e) a fifth section with a decreasing speed;
(f) a sixth section with a negative speed;
(g) a seventh section with an speed increasing from a negative speed toward or to zero.

20. A method for operating a dispenser, the dispenser comprising:
(a) at least a first reservoir and a second reservoir, for containing a first and a second component for a dental material, respectively;
(b) a first and a second plunger driven by a first drive for advancing the first and the second components from the first and the second reservoirs, respectively;
(c) a mixer driven by a second drive for mixing the first and second components to form the dental material from the first and second components; and
(d) a dispensing portion,
wherein the first drive operates based on a first predetermined, non-uniform drive speed profile,
wherein the first predetermined, non-uniform drive speed profile is predetermined before the material is dispensed,
wherein the method comprises:
controlling the first drive according to the first predetermined, non-uniform drive speed profile,
advancing the dental material with the first drive, and
mixing the dental material with the second drive,
wherein the second drive is operated based on a second predetermined, non-uniform drive speed profile, to mix the material,
wherein at least one of the first and second predetermined, non-uniform drive speed profile comprises the following sections for driving at least one of the first drive and second drive:
(a) a first section with an increasing speed starting from 0;
(b) a second section with a peak speed;
(c) a third section with a decreasing speed;
(d) a fourth section with an essentially constant steady state speed;
(e) a fifth section with a decreasing speed;
(f) a sixth section with a negative speed;
(g) a seventh section with an speed increasing from a negative speed toward or to zero.

21. A dispenser, comprising:
(a) at least a first reservoir and a second reservoir, for containing a first and a second component for a dental material, respectively;
(b) a first and a second plunger driven by a first drive for advancing the first and the second components from the first and the second reservoirs, respectively;
(c) a mixer driven by a second drive for mixing the first and second components to form the dental material from the first and second components;
(d) a dispensing portion,
wherein the first drive is configured to operate based on a first predetermined, non-uniform drive speed profile to first advance the first and second components from the first and second reservoirs, then, after advancing the first and second components from the first and second reservoirs, retract the first and second plungers to relieve built-up pressure within the first and the second reservoirs, and, after relieving built-up pressure within the first and the second reservoirs, stop the first and second plungers at positions more advanced than prior to the advance of the first and second components from the first and second reservoirs, and
wherein the first predetermined, non-uniform drive speed profile is predetermined based on the material properties, the properties of the dispenser, the properties of the mixer, or a combination thereof.

22. A dispenser, comprising:
(a) at least a first reservoir and a second reservoir, for containing a first and a second component for a dental material, respectively;
(b) a first and a second plunger driven by a first drive for advancing the first and the second components from the first and the second reservoirs, respectively;
(c) a mixer driven by a second drive for mixing the first and second components to form the dental material from the first and second components; and
(d) a dispensing portion,
wherein the first drive is configured to operate based on a first predetermined, non-uniform drive speed profile to first advance the first and second components from the first and second reservoirs, then, after advancing the first and second components from the first and second reservoirs, retract the first and second plungers to relieve built-up pressure within the first and the second reservoirs, and, after relieving built-up pressure within the first and the second reservoirs, stop the first and second plungers at positions more advanced than prior to the advance of the first and second components from the first and second reservoirs, wherein the second drive is configured to operate based on a second predetermined, non-uniform drive speed profile, and wherein the first and second predetermined, non-uniform drive speed profiles are generally proportional.

* * * * *